United States Patent [19]

Pike et al.

[11] 3,954,832

[45] May 4, 1976

[54] 16-AND 16,16-METHYL AND ETHYL SUBSTITUTED $PGA_1$-TYPE COMPOUNDS

[75] Inventors: John E. Pike; William P. Schneider, both of Kalamazoo, Mich.

[73] Assignee: The Upjohn Company, Kalamazoo, Mich.

[22] Filed: Feb. 11, 1974

[21] Appl. No.: 441,648

Related U.S. Application Data

[60] Division of Ser. No. 274,822, July 24, 1972, Pat. No. 3,813,433, and a continuation-in-part of Ser. No. 123,388, March 11, 1971, abandoned, which is a continuation-in-part of Ser. No. 648,992, June 26, 1969, abandoned.

[52] U.S. Cl. ........................ 260/468 D; 260/211 R; 260/247.2 R; 260/268 R; 260/293.65; 260/326.2; 260/424.9; 260/439 R; 260/448 R; 260/501.1; 260/501.1 S; 260/501.17; 260/501.2; 260/514 D

[51] Int. Cl.² .................... C07C 61/38; C07C 69/74

[58] Field of Search................ 260/468 D, 514 D

[56] References Cited
UNITED STATES PATENTS 3,514,383  5/1970  Real .................................. 204/158

FOREIGN PATENTS OR APPLICATIONS 772,584  3/1972  Belgium ........................... 260/468

OTHER PUBLICATIONS

Ramwell et al., Nature 221, 1251, (1969).

Primary Examiner—Robert Gerstl
Attorney, Agent, or Firm—Morris L. Nielsen

[57] ABSTRACT

Prostaglandin $E_1$-type, $F_1$-type, $A_1$-type, and $B_1$-type compounds with one or two methyl or ethyl substituents at the C-16 position are disclosed. These are useful for the same pharmacological purposes as the unsubstituted prostaglandins.

6 Claims, No Drawings

16-AND 16,16-METHYL AND ETHYL SUBSTITUTED PGA₁-TYPE COMPOUNDS

CROSS REFERENCE TO RELATED APPLICATIONS

This application is a division of our copending application Ser. No. 274,822, filed July 24, 1972, now issued as U.S. Pat. No. 3,813,433, which is a continuation-in-part of our then copending application Ser. No. 123,388, filed Mar. 11, 1971, now abandoned, which was a continuation-in-part of our then copending application Ser. No. 648,992, filed June 26, 1967, now abandoned.

DESCRIPTION OF THE INVENTION

This invention relates to compositions of matter, and to methods and intermediates for producing them. In particular, the several aspects of this invention relate to novel analogs of some of the known prostaglandins, for example, prostaglandin $E_1$ ($PGE_1$), prostaglandin $F_1$ ($PGF_{1\alpha}$ and $PGF_{1\beta}$), prostaglandin $A_1$ ($PGA_1$), and prostaglandin $B_1$ ($PGB_1$).

Each of the above-mentioned known prostaglandins is a derivative of prostanoic acid which has the following structure and atom numbering:

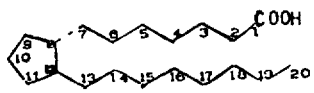

I

A systematic name for prostanoic acid is 7-[(2β-octyl)-cyclopent-1α-yl]heptanoic acid.

$PGE_1$ has the following structure:

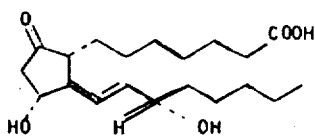

II $PGF_{1\alpha}$ has the following structure:

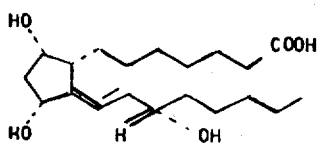

III $PGF_{1\beta}$ has the following structure:

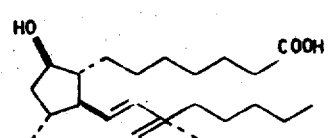

IV $PGA_1$ has the following structure:

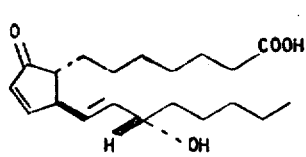

V $PGB_1$ has the following structure:

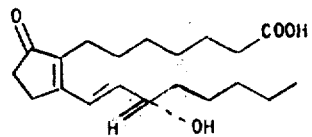

VI

The prostaglandin formulas mentioned above each have several centers of asymmetry. Each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In formulas I, II, III, IV, V and VI, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. The side-chain hydroxy at C-15 in Formulas II to VI is in S (α) configuration.

Each of the novel prostanoic acid analogs of this invention is encompassed by the following formula or by the combination of that formula and its mirror image:

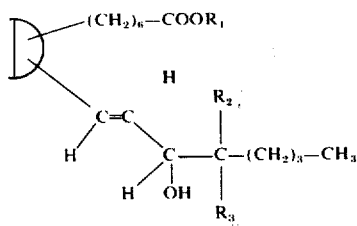

VII wherein 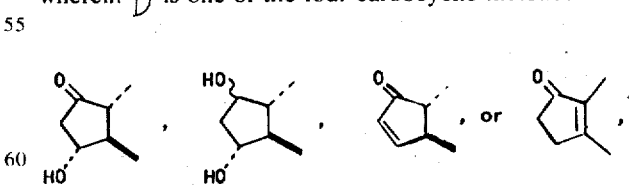 is one of the four carbocyclic moieties:

wherein ~ indicates alpha or beta attachment of hydroxyl to the cyclopentane ring, wherein $R_1$ is hydrogen, alkyl of one to 8 carbon atoms, inclusive, or a pharmacologically acceptable cation, and wherein $R_2$ and $R_3$ are hydrogen, methyl, or ethyl, provided that at least one of $R_2$ and $R_3$ is not hydrogen.

Formula VII, which is written in generic form for convenience, represents PGE₁-type compounds when D is

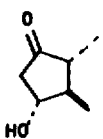

PGF₁α-type compounds when D is

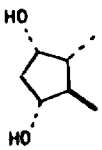

PGF₁β-type compounds when D is

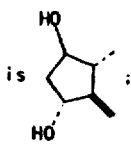

PGA₁-type compounds when D is

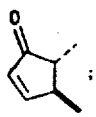

and PGB₁-type compounds when D is

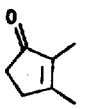

In Formula VII, the configuration of the hydroxyl at C-15 is alpha as in the known prostaglandins of Formulas II to VI. Furthermore, the substituents on the $C_{13}-C_{14}$ carbon-carbon double bond are always in trans configuration.

Each of the novel prostanoic acid analogs of this invention has one or two alkyl substituents at C-16, i.e. the carbon atom adjacent to the hydroxyl-substituted C-15 carbon atoms. Thus, these novel prostanoic acid analogs may be conveniently designated 16-methyl-prostaglandins, 16-ethyl-prostaglandins, 16,16-dimethyl-prostaglandins, 16,16-diethyl-prostaglandins, or 16-methyl-16-ethyl-prostaglandins, e.g. 16-methyl-PGE₁, 16-ethyl-PGF₁α, 16,16-dimethyl-PGF₁β, 16,16-diethyl-PGA₁, 16-methyl-16-ethyl-PGB₁, and the like.

Like the natural prostaglandins described above, these novel 16- or 16,16-di-substituted prostaglandin analogs have several centers of asymmetry. In addition to those found in the natural prostaglandins, there is an asymmetric center at C-16 when that carbon atom is mono-substituted as in the 16-methyl or 16-ethyl PG compounds. 16-Methyl-PGE₁, therefore, has two C-16 epimers, both having the same configuration at the other asymmetric centers as that of natural PGE₂, i.e. alpha for the side chain at C-8 and alpha for the hydroxyls at C-11 and C-15.

With regard to Formula VII, examples of alkyl of one to 8 carbon atoms, inclusive, are methyl, ethyl, propyl, butyl, pentyl, hexyl, heptyl, octyl, and isomeric forms thereof.

As in the case of Formulas II to VI, Formula VII is intended to represent optically active prostanoic acid analogs with the same absolute configuration as PGE₁ obtained from mammalian tissues. The novel prostanoic acid derivatives of this invention also include the corresponding racemic compounds. Formula VII plus its mirror image are necessary in combination to describe a racemic compound. For convenience hereinafter, when the word "racemic" precedes the name of one of the novel prostanoic acid derivatives of this invention, the intent is to designate a racemic compound represented by the combination of the appropriate Formula VII and the mirror image of that formula. When the word "racemic" does not precede the compound name, the intent is to designate an optically active compound represented only by the appropriate formula VII and with the same absolute configuration as PGE₁ obtained from animal tissues.

PGE₁, PGF₁α, PGF₁β, PGA₁, and PGB₁, and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, PGF₁β, and PGA compounds as measured, for example, in anesthetized (pentobarbital sodium) pentolinium-treated rats with indwelling aortic and right heart cannulas; pressor activity, similarly measured, for the PGF₁α compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, $PGF_\alpha$, $PGF_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breating in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and predinisolone). Regarding use of these compounds see South African Pat. No. 681,055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF $\alpha$, and PGF $\beta$ compounds are especially useful as additives to blood, blood products, blood substituents, and other fluids which are used in artifical extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animals, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g. oxytocin, and the various ergot alkaloids including derivatives and analogs thereof. Therefore, $PGE_2$, for example, is useful in place of or in combination with less then usual amounts of these known smooth muscle stimulators, for example, to relieve the symptoms of paralytic ileus, or to control or prevent atonic uterime bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGA, and PGF $\beta$ compounds are useful as hypotensive agents to reduce blood pressure in mammals, including man. For this purpose, the compounds are administered by intravenous infusion at the rate about 0.01 to about 50 μg. per kg. of body weight per minute, or in single or multiple doses of about 25 to 500 μg. per kg. of body weight total per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGE$_1$ or PGF$_{1\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excess or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methyl prednisolone, and fluprednisolone, each of those being used in the combination at the usual concentration suitable for its use alone.

The novel Formula-VII 16-alkyl- and 16,16-dialkyl-PGE$_1$, -PGF$_{1\alpha}$, -PGF$_{1\beta}$, -PGA$_1$, and -PGB$_1$ compounds each cause the biological responses described above for the PGE, PGF$_\alpha$, PGF$_\beta$, PGA, and PGB compounds, respectively, and each of these novel compounds is accordingly useful for the above-described corresponding purposes, and is used for those purposes in the same manner as described above.

The known PGE, PGF$_\alpha$, PGF$_\beta$, PGA, and PGB compounds uniformly cause multiple biological responses even at low doses. For example, PGE$_1$ causes vasodepression and smooth muscle stimulation at the same time it exerts antilipolytic activity. Moreover, for many applications, these known prostaglandins have an inconveniently short duration of biological activity. In striking contrast, the novel prostaglandin analogs of Formula VII are substantially more specific with regard to potency in causing prostaglandin-like biological responses, and have a substantially longer duration of biological activity. Therefore, each of these novel prostaglandin analogs is useful in place of one of the corresponding above-mentioned known prostaglandins for at least one of the pharmacological purposes indicated above for the latter, and is surprisingly and unexpectedly more useful for that purpose because it has a different and narrower spectrum of biological activity than the known prostaglandin, and therefore is more specific in its activity and causes smaller and fewer undesired side effects than the known prostaglandin. Moreover, because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, bucally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 16-alkyl and 16,16-dialkyl $PGE_1$, $PGF_{1\alpha}$, $PGF_{1\beta}$, $PGA_1$, and $PGB_1$ type compounds encompassed by Formulas VII are used for the purposes described above in the free acid form, in ester form, or in pharmacologically acceptable salt form. When the ester form is used, the ester is any of those within the above definition of $R_1$. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these Formula-VII compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropyl-pyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amine-2-methyl-1-propanol, tris(hydroxy-methyl)aminomethane, N-phenylethanolamine, N-(p-tert-amylphenyl)-diethanolamine, galactamine, N-methyl-glucamine, N-methylglycosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of Formula VII are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that $R_1$ in the Formula-VII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 16-alkyl and 16,16-dialkyl $PGE_1$, $PGF_{1\alpha}$, $PGF_{1\beta}$, $PGA_1$, and $PGB_1$ type compounds encompassed by Formula VII are produced by the reactions and procedures described and exemplified hereinafter.

The various $PGF_{1\alpha}$-type and $PGF_{1\beta}$-type compounds encompassed by Formula VII are prepared by carbonyl reduction of the corresponding PGE type compounds. For example, carbonyl reduction of 16-methyl-$PGE_1$ gives a mixture of 16-methyl-$PGF_{1\alpha}$ and 16-methyl-$PGF_{1\beta}$.

These ring carbonyl reductions are carried out by methods known in the art for ring carbonyl reductions of known prostanoic acid derivatives. See, for example, Bergstrom et al., Arkiv Keml 19, 563 (1963), Acta Chem. Scand. 16, 969 (1962), and British No. 1,097,533. Any reducing agent is used which does not react with carbon-carbon double bonds or ester groups. Preferred reagents are lithium (tri-tert-butoxy) aluminum hydride, the metal borohydrides, especially sodium, potassium and zinc borohydrides, and the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various $PGA_1$-type compounds encompassed by Formula VII are prepared by acidic dehydration of the corresponding PGE type compounds. For example, acidic dehydration of 16-ethyl-$PGA_1$ gives 16-ethyl-$PGA_1$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various 16-alkyl and 16,16-dialkyl $PGB_1$-type compounds encompassed by Formula VII are prepared by basic dehydration of the corresponding PGE type compounds, or by contacting the corresponding PGA type compounds with base. For example, both 16,16-dimethyl-$PGE_1$ and 16,16-dimethyl-$PGA_1$ give 16,16-dimethyl-$PGB_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB type compound.

The various transformations of PGE$_1$-type compounds of Formula VII to the corresponding PGF$_{1\alpha}$, PGF$_{1\beta}$, PGA$_1$, and PGB$_1$ type compounds are shown in Chart A, wherein E represents

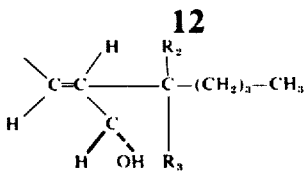

and wherein R$_1$, R$_2$, R$_3$, and ~ are as defined above.

The novel 16-alkyl and 16,16-dialkyl PGE$_1$-type acids and esters of Formula VII are prepared by the sequence of transformations shown in Chart B wherein Formulas VIII, IX, X, XI, and XII include optically active compounds as shown and racemic compounds of those formulas and the mirror image thereof. Also in Chart B, G is -(CH$_2$)$_3$-CH$_3$; R$_2$ and R$_3$ are hydrogen, methyl, or ethyl, provided that at least one of R$_2$ and R$_3$ is not hydrogen; R$_4$ is alkyl of one to 8 carbon atoms, inclusive; R$_5$ is alkyl of one to 5 carbon atoms, inclusive; and ~ indicates attachment to the cyclopropane ring in exo or endo configuration. In Chart B the novel PGE$_1$-type esters of this invention are encompassed by Formula XII.

CHART A

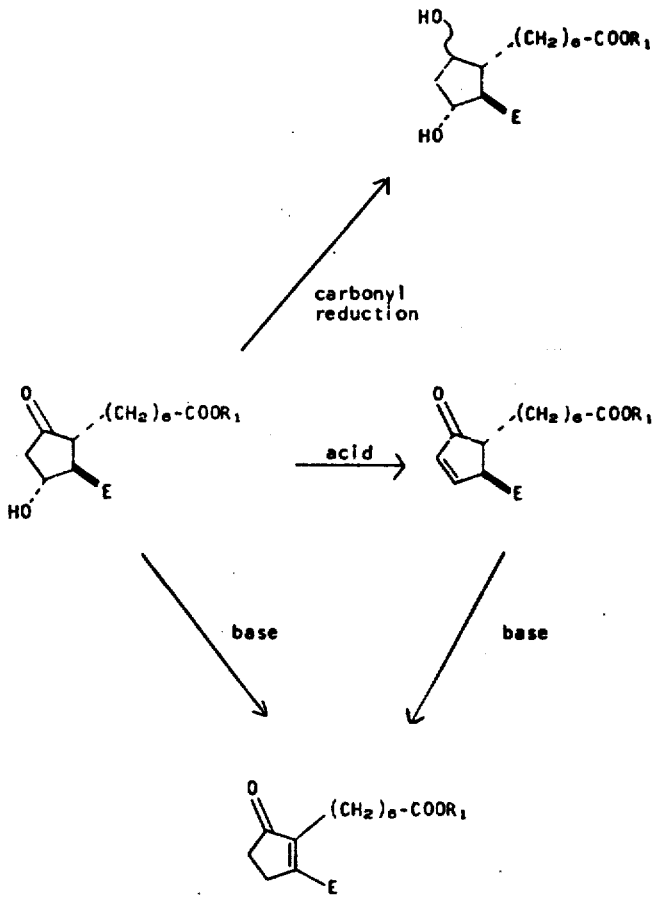

CHART B

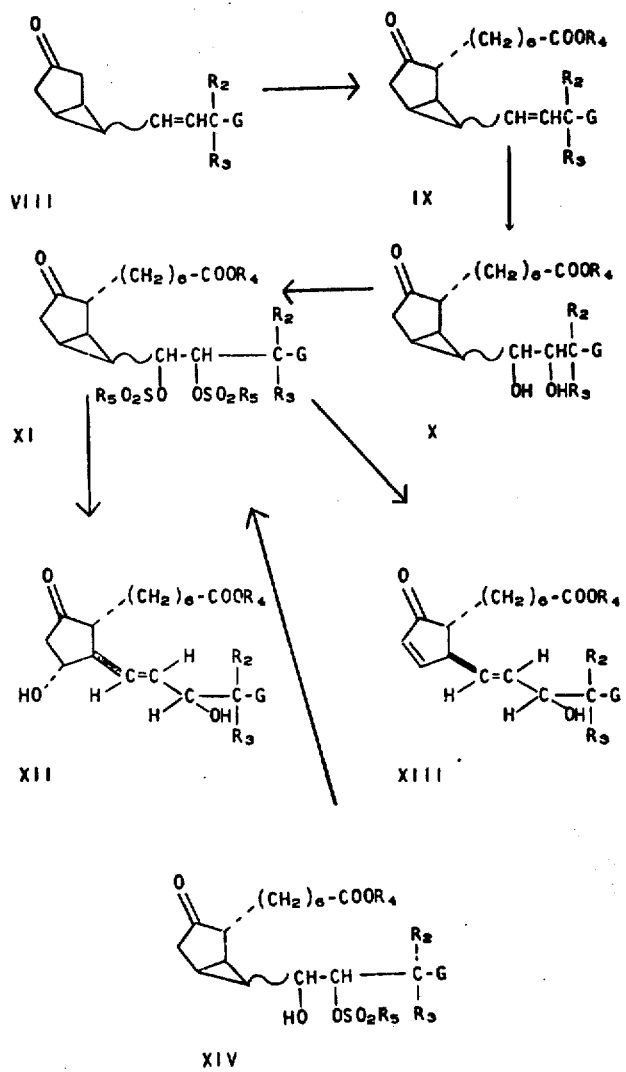

The Formula-VIII bicyclo-ketone reactant of Chart B exists in four isomeric forms, exo and endo with respect to the attachment of the

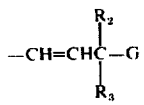

moiety, and cis and trans with respect to the doublel bond in that same moiety. Each of those isomers separately or various mixtures thereof are used as reactants according to this invention to produce substantially the same final PGE or PGA type product mixture.

The process for preparing either the exo or endo configuration of the Formula-VIII bicyclo-ketone is known to the art. See Belgian Pat. No. 702,477; reprinted in Farmdoc Complete Specifications, Book 714, No. 30,905, page 313, Mar. 12, 1968. See West Germany Offenlegungsschrift No. 1,937,912; reprinted in Farmdoc Complete Specifications, Book No. 14, No. 6869 R, Week R₅, Mar. 18, 1970.

In said Belgian Pat. No. 702,477, a reaction sequence capable of forming exo ketone VIII is as follows: The hydroxy of 3-cyclopentenol is protected, for example, with a tetrahydropyranol group. Then a diazoacetic acid ester is added to the double bond to give an exo-endo mixture of a bicyclo[3.1.0]hexane substituted at 3 with the protected hydroxy and at 6 with an esterified carboxyl. The exo-endo mixture is treated with a base to isomerize the endo isomer in the mixture to more of the exo isomer. Next, the carboxylate ester group at 6 is transformed to an aldehyde group. Then, said aldehyde group is transformed by the Wittig reaction, in this case to a moiety of the formula

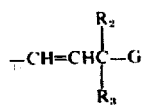

which is in exo configuration relative to the bicyclo ring structure. Next, the protective group is removed to regenerate the 3-hydroxy which is then oxidized, for example, by the Jones reagent, i.e., chromic acid (see J. Chem. Soc. 39 (1946)), to give said exo ketone VIII.

Separation of the cis-exo and trans-exo isomers of VIII is described in said Belgian Pat. No. 702,477. However, as mentioned above, that separation is usually not necessary since the cis-trans mixture is useful as a reactant in the next process step.

The process described in said Belgian Pat. No. 702,477 for producing the exo form of bicyclo-ketone VIII uses, as an intermediate, the exo form of a bicyclo[3.1.0]-hexane substituted at 3 with a protected hydroxy, e.g., tetrahydropyranyloxy, and at 6 with an esterified carboxyl. When the corresponding endo compound is substituted for that exo intermediate, the process in said Offenlegungsschrift No. 1,937,912 leads to the endo form of bicyclo-ketone VIII. That endo compound to be used has the formula:

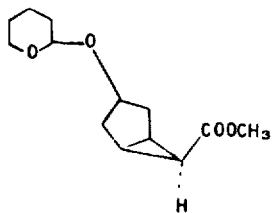

XV

Compound XV is prepared by reacting endo-bicyclo[3.1.0]-hex-2-ene-6-carboxylic acid methyl ester with diborane in a mixture of tetrahydrofuran and diethyl ether, a reaction generally known in the art, to give endo-bicyclo[3.1.0]-hexane-3-ol-6-carboxylic acid methyl ester which is then reacted with dihydropyran in the presence of a catalytic amount of $POCl_3$ to give the desired compound. This is then used as described in said Offenlegungsschrift No. 1,937,912 to produce the endo form of bicyclo-ketone VIII.

As for exo VIII, the above process produces a mixture of endo-cis and endo-trans compounds. These are separated as described for the separation of exo-cis and exo-trans VIII, but this separation is usually not necessary since, as mentioned above, the cis-trans mixture is useful as a reactant in the next process step.

In the processes of said Belgian patent and said Offenlegungsschrift, certain organic halides, e.g., chlorides and bromides, are necessary to prepare the Wittig reagents used to generate the generic moiety —CH=CHC($R_2$)($R_3$)—G of bicyclo-ketone VIII. These organic chlorides and bromides, G—C($R_2$)($R_3$)—CH$_2$—Cl and G—C($R_2$)($R_3$)—CH$_2$—Br, are known in the art or can be prepared by methods known in the art. Those halides not available are prepared by reacting the corresponding primary alcohol G—C($R_2$)$R_3$)—CH$_2$OH with $PCl_3$, $PBr_3$, or any of the other halogenating agents useful for this purpose. Accordingly, there is used 1-bromo-2-methylhexane, 1-bromo-2,2-dimethylhexane, 3-(bromomethyl)heptane, 3-(bromomethyl)-3-ethyl-heptane, and 3-(bromomethyl)-3-methylheptane, or the corresponding chloro compounds, when the desired end-product is, respectively, 16-methyl-PGE$_1$, 16,16-dimethyl-PGE$_1$, 16-ethyl-PGE$_1$, 16,16-diethyl-PGE$_1$, and 16-ethyl-16-methyl-PGE$_1$.

Referring to chart B, bicyclo olefin VIII is transformed to the Formula-IX compound by alkylating with an alkylation agent of the formula Hal—($CH_2$)$_6$—COOR$_4$ wherein $R_4$ is as defined above and Hal is chloro, bromo, or iodo. Any of the alkylation procedures known in the art to be useful for alkylating cyclic ketones with alkyl halides and haloalkanoic esters are used for the transformations of VIII to IX. See, for example, the above-mentioned Belgian Pat. No. 702,477 for procedures useful here and used there to carry out similar alkylations.

For these alkylations, it is preferred that Hal be bromo or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1,2-dimethoxyethane. Otherwise, procedures for producing and isolating the desired Formula-IX compound are within the skill of the art.

These alkylation procedures produce mixtures of alpha and beta alkylation products, i.e., a mixture of Formula-IX products wherein part has the —($CH_2$)$_6$—COOR$_4$ moiety attached in alpha configuration, and wherein part has that moiety attached in beta configuration.

When about one equivalent of base per equivalent of Formula-VIII ketone is used, the alpha configuration usually predominates. These alpha-beta isomer mixtures are separated at this stage or at any subsequent stage in the multi-step processes shown in Chart B. Silica gel chromatography is preferred for this separation.

The transformation of the Formula-IX olefin compound to glycol X is carried out by reacting olefin IX with a hydroxylation reagent. Hydroxylation reagents and precedures for this purpose are known in the art. See, for example, Gunstone, Advances in Organic Chemistry, Vol. 1, pp. 103–147, Interscience Publishers, New York, N.Y. (1960). Various isomeric glycols are obtained depending on such factors as whether olefin IX is cis or trans and endo or exo, and whether a cis or a trans hydroxylation reagent is used. Thus endo-cis olefin IX gives a mixture of two isomeric erythro glycols of Formula X with a cis hydroxylation agent, e.g., osmium tetroxide. Similarly, the endo-trans olefin IX gives a similar mixture of the same two erythro glycols with a trans hydroxylation agent, e.g., hydrogen peroxide. The endo-cis olefins and the endo-trans olefins IX give similar mixtures of two threo glycol isomers with cis and trans hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Chart B to produce final products of formulas XI, and then, according to Chart B to produce the other final products of this invention. Thus, the various isomeric glycol mixtures encompassed by Formula X produced from the various isomeric olefins encompassed by Formula IX are all useful for these same purposes.

Referring again to Chart B, the bis-alkanesulfonic acid ester XI is prepared by reacting glycol IX with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25° C. for several hours. The Formula-XI bis-sulfonic acid ester is then isolated by procedures known in the art.

The transformation of bis-sulfonic acid ester XI to the PGE-type compound XII is carried out by reacting bis-ester XI with water in the range about 0° to about 60° C., preferaably at 25° C., the reaction then proceeding to completion in about 5 to 20 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of Formula-XII isomers which differ in the configuration of the side chain hydroxy, that being either $\alpha$ or $\beta$. These are separated from byproducts and from each other by silica gel chromatography. A usual byproduct is the mono-sulfonic acid ester of Formula XIV (Chart B). This mono-sulfonic acid ester is esterified to the Formula-XI bis-sulfonic acid ester in the same manner described above for the transformation of glycol X to bis-ester XI and thus are recycled back to additional Formula-XII final product.

The transformations of XI (Chart B) to the PGA-type compound XIII is carried out by heating bis-ester XI in the range 40° to 100° C. with a combination of water, a base characterized by its water solution having a pH 8 to 12, and sufficient inert water-soluble organic diluent to form a basic and substantially homogeneous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-ester XI to PGE-type product XII. The same mono-sulfonic acid ester XIV observed as a byproduct in those transformations is also observed during preparation of PGA-type product XIII.

For the transformations of bis-sulfonic acid ester XI to final products XII and XIII, it is preferred to use the bis-mesyl esters, i.e., compound XI wherein $R_5$ is methyl.

The Formula-XII PGE-type compounds and the Formula-XIII PGA-type compounds shown in Chart B are all $R_4$ carboxylic acid esters, wherein $R_4$ is as defined above. Moreover, when those PGE-type and PGA-type $R_4$ esters are used to prepare the other prostaglandin-like compounds according to Chart A, corresponding $R_4$ esters are likely to be produced, especially in the case of the PGF-type compounds. For some of the uses described above, it is preferred that the novel Formula-VII prostaglandin-like compounds of this invention be in free acid form, or in salt form which requires the free acid as a starting material. The PGF-type esters and the PGB-type compounds are easily hydrolyzed or saponified to the free acids by the usual known procedures, especially when $R_1$ ($R_4$) is alkyl of one to 4 carbons, inclusive, preferably methyl or ethyl.

On the other hand, the PGE-type and PGA-type esters are difficult to hydrolyze or saponify without causing unwanted structural changes in the desired acids. There are two other procedures to make the free acid forms of these compounds.

One of those procedures is applicable mainly in preparing the free acids from the corresponding alkyl esters wherein the alkyl group contains one to 8 carbon atoms, inclusive. That procedure comprises subjecting the PG-type alkyl ester to the acylase enzyme system of a microorganism species of Subphylum 2 of Phylum III, and thereafter isolating the acid. See West Germany Offenlegungsschrift No. 1,937,678; reprinted in Farmdoc Complete Specifications, Book No. 13, No. 6863 R, Week R5, Mar. 18. 1970.

Another procedure for making the free acids of the PGE-type and PGA-type Formula-VIII compounds involves treatment of certain haloethyl esters of those acids with zinc meal and an alkanoic acid of 2 to 6 carbon atoms, preferably acetic acid. Those haloethyl esters are the esters wherein $R_1$ is ethyl substituted in the $\beta$-position with 3 chloro, 2, or 3 bromo, or one, 2, or 3 iodo. of those haloethyl moieties, $\beta, \beta, \beta$-trichloroethyl is preferred. Zinc dust is preferred as the physical form of the zinc. Mixing the haloethyl ester with the zinc dust at about 25° C. for several hours usually causes substantially complete replacement of the haloethyl moiety of the Formula-VII PGE- or PGA-type ester with hydrogen. The free acid is then isolated from the reaction mixture by procedures known to the art. This procedure is also applicable to the production of Formula-VII PGF-type and PGB-type free acids.

Formula-IX olefins wherein $R_4$ is haloethyl as above defined are necessary as intermediates for this route to the final PGE, PGF, PGA, and PGB type free acids. These haloethyl ester intermediates can be prepared by alkylation of olefin VIII (Chart B) with the appropriate alkylating agent of the formula $Hal(CH_2)_6$—COOR$_4$ wherein $R_4$ is haloethyl as above defined. However, preferred routes to the Formula-IX haloethyl ester intermediates are shown in Chart C In Chart C, G, $R_2$, $R_3$, and ~ are as defined above. Haloethyl represents ethyl substituted in the $\beta$-position with 3 chloro, 2 or 3 bromo, or 1, 2, or 3 iodo, preferably —$CH_2CCl_3$. $R_6$ represents alkyl of one to 4 carbon atoms, inclusive, preferably methyl or ethyl.

Compound XV in Chart C is within the scope of compound IX in Chart B. Ketone XV is reduced to the corresponding hydroxy compound XVI with a carbonyl reducing agent, e.g., sodium borohydride, as described above in discussion of Chart A. Then, hydroxy ester XVI is saponified by known procedures to hydroxy acid XVII. This hydroxy acid is transformed to keto haloethyl ester XX by oxidation of the hydroxy group to keto and esterification of the carboxyl group to —COO—haloethyl. As shown in Chart C, these two reactions are carried out in either order.

CHART C

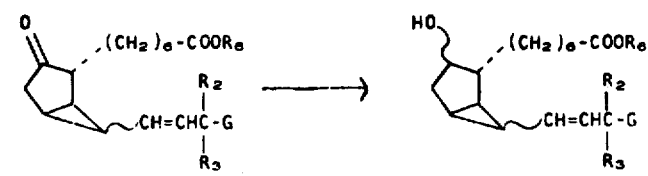

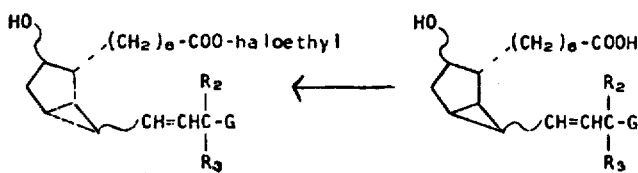

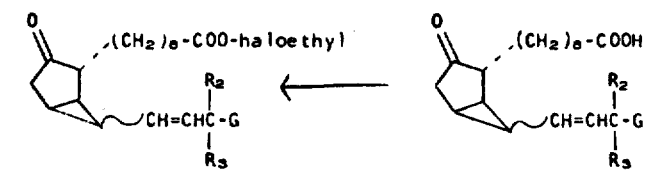

However, it is preferred to oxidize first and then esterify.

Hydroxy acid XVII is oxidized to keto acid XIX and hydroxy haloester XVIII are oxidized to keto haloester XX by reaction with an oxidizing agent which does not attack other parts of these molecules, especially the ethylenic linkage of compounds XVII and XVIII. An especially useful reagent for this purpose is the Jones reagent, i.e., acidic chromic acid. Acetone is a suitable diluent for this purpose, and a slight excess of oxidant and temperatures at least as low as about 0° C., preferably about −10° to about −20° C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Soc. 87, 5661 (1965).

Haloethyl esters XVIII and XX are prepared by reacting acids XVII and XIX, respectively, with the appropriate haloethanol, e.g., $\beta,\beta,\beta$-trichloroethanol, in the presence of a carbodiimide, e.g., dicyclohexylcarbodiimide, and a base, e.g., pyridine, preferably in the presence of an inert liquid diluent, e.g., dichloromethane, for several hours at about 25° C.

As discussed above, the processes of Charts A and B, also utilizing the intermediates of Chart C, lead either to acids ($R_1$ is hydrogen) or to alkyl esters ($R_1$ or $R_4$ is alkyl of one to 8 carbon atoms, inclusive). When a Formula-VII $PGE_1$- or $PGF_1$-type acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

An alternative method for esterification of the carboxyl moiety of the PGF-type or PGE-type compounds comprises transformation of the free acid to the corresponding silver salts, followed by interaction of the salt with an alkyl iodide. Examples of suitable iodides are methyl iodide, ethyl iodide, butyl iodide, isobutyl iodide, tertbutyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final Formula-VII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the Formula-VII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the Formula-VII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporaton. If the amine is relatively volatile, any excess can easily be removed by evaporation. It is preferred to use stoichiometric amounts of the less volatile amines.

Salts wherein the cation is quaternary ammonium are produced by mixing the Formula-VII acid with the stoichiometric amount of the corresponding quaternary ammonium hydroxide in water solution, followed by evaporation of the water.

When the optically active final compound is desired, it is made by resolution of the racemic compound or by resolution of one of the asymmetric racemic intermediates. These resolutions are carried out by procedures known in the art. For example, when final compound VII is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of Formula VII is then obtained by treatment of the salt with an acid by known general procedures. Alternatively, the free acid form of olefin IX or glycol X is resolved into separate d and l forms and then esterified and transformed further to the corresponding optically active form of the final product VII as described above.

Alternatively, glycol reactants X, in exo or endo form, are transformed to ketals with an optically active 1,2-glycol, e.g., D-(—)-2,3-butanediol, by reaction of said 1,2-glycol with the Formula-X compound in the presence of a strong acid, e.g., p-toluenesulfonic acid. The resulting ketal is a mixture of diastereoisomers which is separated into the d and l diastereoisomers, each of which is then hydrolyzed with an acid, e.g., oxalic acid, to the original keto compound, now in optically active form. These reactions involving optically active glycols and ketals for resolution purposes are generally known in the art. See, for example, Chem. Ind. 1664 (1961) and J. Am. Chem. Soc, 84, 2938 (1962). Dithiols may be used instead of glycols.

The optically active and racemic forms of 16-methyl-PGE$_1$ and -PGF$_{1\alpha}$, 16,16-dimethyl-PGE$_1$ and -PGF$_{1\alpha}$, 16-ethyl-PGE$_1$ and -PGF$_{1\alpha}$, 16,16-diethyl-PGE$_1$ and -PGF$_{1\alpha}$, and 16-ethyl-16-methyl-PGE$_1$ and -PGF$_{1\alpha}$ are also prepared by the processes set forth and described in our copending application Ser. No. 648,991, filed June 26, 1967, now issued as U.S. Pat. No. 3,514,383. Those processes use as initial reactants, all-cis 16-methyl-8,11,14-eicosatrienoic acid to produce the 16-methyl prostaglandin analogs, and all cis 16,16-dimethyl-8,11,14-eicosatrienoic acid to produce the 16,16-dimethyl prostaglandin analogs. The preparation of all cis 15-methyl-8,11,14-eicosatrienoic acid is set forth and described in said issued patent. Use of 2-methylhexanone in place of the 2-heptanone used as initial reactant in that process leads to all-cis 16-methyl-8,11,14-eicosatrienoic acid. Likewise, 2,2-dimethylhexanone leads to 16,16-dimethyl-8,11,14-eicosatrienoic acid; 2-ethylhexanone leads to 16-ethyl-8,11,14-eicosatrienoic acid; 2,2-diethylhexanone leads to 16,16-diethyl-8,11,14-eicosatrienoic acid; and 2-ethyl-2-methylhexanone leads to 16-ethyl-16-methyl-8,11,14-eicostrienoic acid.

As set forth and described in said issued patent, all-cis 16-methyl-8,11,14-eicosatrienoic acid and all-cis 16,16-dimethyl-8,11,14-eicosatrienoic acid are each transformed to racemic 16-methyl-PGE$_1$ or racemic 16-methyl-PGF$_{1\alpha}$ and to racemic 16,16-dimethyl-PGE$_1$ or racemic 16,16-dimethyl-PGF$_{1\alpha}$, respectively, by reacting said acids with singlet oxygen and then treating the resulting product with a reducing agent to produce PGF$_\alpha$ -type derivatives or with a mild reducing agent and then with a base, a metal ion catalyst, or with ultraviolet light to produce the PGE-type derivatives.

Likewise, following the procedures of said issued patent, all-cis 16-ethyl-8,11,14-eicosatrienoic acid is transformed to racemic 16-ethyl-PGE$_1$ or racemic 16-ethyl-PGF$_{1\alpha}$ ; all-cis 16,16-diethyl-8,11,14-eicosatrienoic acid is transformed to racemic 16,16-diethyl-PGE$_1$ or racemic 16,16-diethyl-PGF$_{1\alpha}$ ; and all-cis 16-ethyl-16-methyl-8,11,14-eicosatrienoic acid is transformed to racemic 16-ethyl-16-methyl-PGE$_1$ or racemic 16-ethyl-16-methyl-PGF$_{1\alpha}$ .

The optically active prostaglandin analogs, 16-methyl-PGE$_1$, 16-methyl-PGF$_{1\alpha}$ , 16,16-diemethyl-PGE$_1$, and 16,16-dimethyl-PGF$_{1\alpha}$ are prepared as set forth and described in said issued patent by resolution of the corresponding racemic forms prepared as described above. Likewise, following the procedures of said issued patent, the optically active analogs, 16-ethyl-$PGE_1$, 16-ethyl-$PGF_{1\alpha}$, 16,16-diethyl-$PGE_1$, 16,16-diethyl-$PGF_{1\alpha}$, 16-ethyl-16-methyl-$PGE_1$, and 16-ethyl-16-methyl-$PGF_{1\alpha}$ are prepared by resolution of the racemic forms. Alternatively, as set forth and described in said issued patent, optically active 16-methyl and 16,16-dimethyl analogs are prepared by aerobic incubation of all-cis 16-methyl-8,11,14-eicosatrienoic acid or all-cis 16,16-dimethyl-8,11,14-eicosatrienoic acid with comminuted sheep vesicular gland tissue or with the enzyme system contained therein, in a substantially aqueous medium. Likewise, following the procedures of said issued patent, the optically active 16-ethyl, 16,16-diethyl, and 16-ethyl-16-methyl analogs are also prepared. For additional procedural details, see also U.S. Pat. No. 3,296,091, Kupiecki, Life Sciences, 4, 1811 (1965), Struijk, Rec. Trav. Chim. 85, 1233 (1966), and Nugteren et al., Rec. Trav. Chim., 85, 405 (1966).

These biological oxidations produce mixtures of the $PGE_1$ and $PGF_{1\alpha}$ forms of the 16-methyl analogs. Likewise, there are produced mixtures of the $PGE_1$ and $PGF_{1\alpha}$ forms of the 16,16-diemethyl, of the 16-ethyl, of the 16,16-diethyl, and of the 16-ethyl-16-methyl analogs, respectively. The components of each of these mixtures are separated and each component is purified as set forth in U.S. Pat. No. 3,296,091, or by other procedures known to be useful for separating mixtures of the known prostaglandins and purifying the individual components. In particular, advantage is taken of the greater polarity of the $PGF_{1\alpha}$ -type compound in comparison with the $PGE_1$-type compound in these separations, using chromatography on acid-washed silica gel, reversed-phase partition chromatography, preparative thin-layer chromatography, or countercurrent distribution, or a combination of those.

The invention can be more fully understood by the following examples and preparations:

All temperatures are in degrees centigrade.

"Brine" as used herein refers to aqueous saturated sodium chloride solution.

DESCRIPTION OF THE PREFERRED EMBODIMENTS

EXAMPLE 1

Racemic 16-Methyl-$PGE_1$ Methyl Ester (Formula VII: D is

$R_1$ and $R_3$ are methyl; and $R_2$ is hydrogen).

Refer to Chart B. There is first prepared the Formula-VIII olefin wherein $R_2$ is hydrogen, $R_3$ is methyl, and G is -$(CH_2)_3CH_3$. Endo-bicyclo[3.1.0]hexan-3-ol-6-carboxaldehyde 3-tetrahydropyranyl ether (100 g) is reacted with (2-methylhexyl)triphenylphosphonium bromide, obtained from racemic 1-bromo-2-methylhexane, following the procedure disclosed in West Germany Offeniegungsschrift No. 1,937,912 cited above. Thereafter, following the procedures disclosed therein, the Formula-VIII olefin wherein $R_2$ is hydrogen and $R_3$ is methyl is obtained and then isolated by silica gel chromatography.

There is next prepared the Formula-IX compound. To a stirred solution of the Formula-VIII olefin above (10.0 g.) and methyl 7-iodoheptanoate (12 g.) in 250 ml. of tetrahydrofuran under nitrogen at 20° C. is added dropwise a solution of potassium tert-butoxide (7.0 g.) in 500 ml. of nitrogen-purged tetrahydrofuran, over a period of 45 min. The resulting mixture is acidified at once with about 120 ml. of 5% hydrochloric acid, and then concentrated under reduced pressure below 40°C. Water (400 ml.) is added to the residue, and the mixture is extracted with successive 400-ml. portions of diethyl ether. The ether extract is washed with water, then with brine, dried over sodium sulfate, and then evaporated to leave a residue containing the Formula-IX compound, viz. methyl 7-[endo-6-(3-methyl-1-heptenyl)-3-oxobicyclo[3.1.0]hex-2α-yl]heptanoate, as a mixture of two pairs of racemates.

There is next prepared the Formula-X glycol. A solution of the Formula IX racemates above (10 g.) in 160 ml. of tetrahydrofuran is stirred at 50° C. under nitrogen and osmium tetroxide (1.0 g.) is added followed by a solution of potassium chlorate (6.5 g) in 75 ml. of water. Stirring is continued at 50° C. for 3 hrs.; then the tetrahydrofuran is removed by evaporation under reduced pressure and the residue is extracted with methylene chloride. The organic layer is washed with water, dried over sodium sulfate, and evaporated to give a mixture of Formula-X glycols. This mixture of glycols is chromatographed over 2 kg. of silica gel wet-packed with 15% ethyl acetate in Skellysolve B, eluting successively with 15%, 25%, 35%, 60%, and 80% ethyl acetate in Skellysolve B (isomeric hexanes). Those fractions of eluate shown by TLC (thin layer chromatography) to contain the desired glycols are combined and then evaporated to give the Formula-X product wherein $R_2$ is hydrogen and $R_3$ is methyl, as a mixture of isomeric glycols.

The above glycol mixture (7.1 g.) is dissolved in 90 ml. of pyridine and stirred at 0° C. under nitrogen while 8.5 ml. of methanesulfonyl chloride is added over a period of 15 min. The mixture is stirred at 0° C. for 2.5 hrs., then cooled to −15° C. and 10 ml. of ice and water is added slowly. After 5 min. additional stirring at −5° to 0° C. the mixture is poured into 500 ml. of ice and water. Cold 1:3 dichloromethane-ether (200 ml.) is added, followed by 360 ml. of cold 3M. hydrochloric acid, and the mixture is extracted rapidly with methylene chloride-ether. The organic extracts are washed with 2% sulfuric acid, water, aqueous bicarbonate, and brine, then dried over sodium sulfate and evaporated to give the Formula-XI bismethanesulfonate.

The above bismesylate of the mixed glycols (10.5 g.) is dissolved in 400 ml. of 2:1 acetone-water and allowed to stand about 18 hrs. at 25° C., then is diluted with 400 ml. of water and the acetone is removed by evaporation under reduced pressure. The aqueous residue is extracted with ethyl acetate and the extracts are washed with aqueous sodium bicarbonate and brine, then dried over sodium sulfate and evaporated to give a mixture of isomeric Formula-XII products. The residue contains four racemates, i.e. four pairs of isomeric Formula-XII products having different asymmetric centers at C-8, C-15 and C-16. The following procedures are directed toward the separation of the racemates. Two of these racemates are similar in being more polar than the other two racemates, and are separated from the other two by means of silica gel chromatography.

The residue is chromatographed over 1.6 kg. of silica gel wet-packed with 30% ethyl acetate in Skellysolve B, eluting with 8 l. of 30%, 4 l. of 40%, 13 l. of 60%, and 16 l. of 80% ethyl acetate in Skellysolve B, 10 l. of ethyl acetate, then gradient elution with 5 l. of ethyl acetate, and 5 l. of 5% methanol in ethyl acetate, collecting 500 ml. fractions. Those fractions shown by TLC to contain the two more polar (slower eluting) racemates are combined and concentrated.

These mixed racemates have the natural prostaglandin configuration at C-8 and C-15, viz. R and S respectively, and differ in their stereochemistry at C-16. To separate then, the Formula-XII product is transformed to the bis(trimethylsilyl)ether. A solution of the Formula-XII product (5.0 g.), hexamethyldisilazane (25 ml.), and trimethyl-chlorosilane (10 ml.) in 20 ml. of tetrahydrofuran is left standing at about 25° C. for 20 hours. The mixture is filtered through a bed of diatomaceous earth and the filtrate is concentrated by evaporation under reduced pressure.

The residue is chromatographed over 1.6 kg. of silica gel wet-packed with 30% ethyl acetate in Skellysolve B, eluting with 8 l. of 30%, 4 l. of 40%, 13 l. of 60%, and 16 l. of 80% ethyl acetate in Skellysolve B, 10 l. of ethyl acetate, then gradient elution with 5 l. of ethyl acetate, and 5 l. of 5% methanol in ethyl acetate, collecting 500 ml. fractions.

Those fractions shown by TLC to contain the separated silylated racemates, free of intermediates and by-products, are combined and concentrated. The trimethylsilyl groups are replaced with hydrogen by contacting each residue with a solution of 50 ml. of methanol and 20 ml. of water at 25° C. for 16 hrs., thereafter removing solvents under reduced pressure to yield the racemic Formula-XII title compounds. Those racemates shown to have more biological activity in smooth muscle strip tests (see J. R. Weeks et al, Journal of Applied Physiology 25, (No. 6), 783 (1968)) are more useful for the above-described purposes.

Following the procedures of Example 1, but replacing the Formula-VIII compound of that example with the Formula-VIII compound wherein $R_2$ is hydrogen and $R_3$ is ethyl, there are obtained the corresponding racemic 16-ethyl-$PGE_1$ products.

Following the procedures of Example 1, but replacing the Formula-VIII compound of that example with the Formula-VIII compound wherein $R_2$ and $R_3$ are both methyl, there is obtained the corresponding 16,16-dimethyl-$PGE_1$ racemic product. For these di-16-substituted compounds the final step above, utilizing chromatography of the silylated product, may be omitted because of the absence of an asymmetric center at C-16.

Likewise replacing the Formula-VIII compound of Example 1 with the Formula-VIII compounds wherein $R_2$ and $R_3$ are ethyl, and wherein $R_2$ is ethyl and $R_3$ is methyl, there are obtained the corresponding 16,16-diethyl- and 16-ethyl-16-methyl-$PGE_1$ compounds, respectively.

Following the procedures of Example 1 but employing Formula-IX compounds wherein $R_4$ is alkyl of 2 to 8 carbon atoms, inclusive, instead of methyl, there are obtained the corresponding $PGE_1$-type compounds wherein $R_4$ is alkyl of 2 to 8 carbon atoms.

EXAMPLE 2

7-[Endo-6-(3-methyl-1-heptenyl)-3-oxobicyclo[3.1.0]hex-2α-yl]heptanoic Acid, Trichloroethyl Ester (Formula XX, Chart C: G is -(CH$_2$)$_3$CH$_3$; haloethyl is —CH$_2$CCl$_3$; $R_2$ is hydrogen; $R_3$ is methyl; and ~ is endo).

Refer to Chart C. The Formula-XV compound, i.e. the Formula-IX compound of Example 1 as the methyl ester, is reduced with sodium borohydride to the Formula-XVI compound as follows. To a solution of the Formula-XV compound (4.0 g.) in 110 ml. of absolute ethanol at 0° C. is added a solution of sodium borohydride (1.5 g.) in 10 ml. of water, with stirring. After stirring for 2.5 hrs. at 0°–5° C., about 40 ml. of acetone is added, and, after 5 min., the mixture is evaporated under reduced pressure. The residue is extracted with dichloromethane, and the extract is washed successively with dilute hydrochloric acid and brine, dried, and evaporated to give the Formula-XVI compound.

This ester is dissolved in a mixture of methanol (100 ml.) and 45% aqueous potassium hydroxide solution (30 ml.), and the solution is stirred under nitrogen at 25° C. for 15 hrs. Two volumes of water are then added, and the mixture is acidified with cold hydrochloric acid and then extracted with a mixture of dichloromethane and diethyl ether (1:3). The extract is washed with brine, dried, and evaporated to give the Formula-XVII hydroxy acid.

Jones reagent (7 ml. of a solution of 21 g. of chromic anhydride, 60 ml. of water, and 17 g. of concentrated sulfuric acid) precooled to 0° C., is added dropwise to a solution of this hydroxy acid in 120 ml. of acetone at 0° C. The mixture is stirred 5 min. at 0° C. Then, 5 volumes of water are added, and the mixture is extracted with a mixture of dichloromethane and diethyl ether (1:3). The extract is washed successively with dilute hydrochloric acid and brine, dried, and evaporated to give the Formula-XIX 3-oxo compound.

To a solution of the above Formula-XIX free acid (2.0 g) in 100 ml. of dichloromethane are added, successively, β,β,β-trichloroethanol (25 ml.), pyridine (15 ml.), and dicyclohexylcarbodiimide (4.0 g.). This mixture is stirred 3 hrs. under nitrogen at 25° C. Water (50 ml.) is then added, and the mixture is stirred 10 min. The dichloromethane is evaporated under reduced pressure, and the residue is extracted repeatedly with ethyl acetate. The combined extracts are washed with ice-cold 3 N hydrochloric acid. Then, the extracts are washed successively with aqueous sodium bicarbonate solution and brine, dried, and evaporated under reduced pressure. The residue is chromatographed on 600 g. of silica gel, eluting with 10 l. of a 20–100% ethyl acetate-Skellysolve B gradient, collecting 250-ml. fractions. The fractions shown by TLC to contain the desired product free of starting materials and by-products are combined and evaporated under reduced pressure to yield the Formula-XX title compound, i.e., the trichloroethyl ester.

Following the procedure of Example 2, but using in place of the Formula-XV 3-oxobicyclo[3.1.0]hexane ester, each of the endo and exo Formula-IX intermediates after Example 1, there are obtained the corresponding β,β,β-trichloroethyl esters of those 3-oxobicyclo[3.1.0]hexane acids. Thus, instead of the 3-methyl Formula-XX heptanoates, there are obtained the 3,3-dimethyl, 3-ethyl, 3,3-diethyl, and 3-ethyl-3- methyl Formula-XX heptanoates as trichloroethyl esters.

EXAMPLE 3

Racemic 16-Methyl-PGE$_1$ (Formula VII: ⟩ is

R$_1$ and R$_2$ are hydrogen; and R$_3$ is methyl).

Refer to Chart B. Following the procedures of Example 1 but replacing the Formula-IX methyl ester compound used therein with the Formula-XX trichloroethyl ester compound of Example 2, there is obtained the corresponding racemic 16-methyl-PGE$_1$ trichloroethyl ester.

Zinc dust (420 mg.) is added to a solution of this $\beta,\beta,\beta$-trichloroethyl ester (100 mg.) in 5 ml. of a mixture of acetic acid and water (9:1 v/v). This mixture is stirred under nitrogen 2 hrs. at 25° C. Ethyl acetate (4 volumes) is then added, followed by addition of one N. hydrochloric acid (one volume). The ethyl acetate layer is separated, washed with water and then with brine, dried, and evaporated. The residue is chromatographed on 15 g. of acid-washed silica gel (Silicar CC4), and eluted with 100 ml. of 50%, 100 ml. of 80%, and 200 ml. of 100% ethyl acetate in Skellysolve B, collecting 20-ml. fractions. The fractions containing 16-methyl-PGE$_1$ and no starting material or dehydration products as shown by TLC are combined and evaporated to give the Formula-VII title compound.

Following the procedures of Examples 3 and 1, each of the haloethyl ester Formula-XX intermediates of Example 2 are transformed to the corresponding racemic haloethyl ester PGE$_1$-type compound and thence to the corresponding racemic free acid. There is thus obtained racemic 16,16-dimethyl-PGE$_1$, 16-ethyl-PGE$_1$, 16,16-diethyl-PGE$_1$, and 16-ethyl-16-methyl-PGE$_1$.

EXAMPLE 4

Racemic 16-Methyl-PGF$_{1\alpha}$ and 16-Methyl-PGF$_{1\beta}$ (Formula VII: ⟩ is

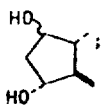

R$_1$ and R$_2$ are hydrogen; R$_3$ is methyl, and ~ is alpha or beta).

Refer to Chart A. A solution of racemic 16-methyl-PGE$_1$ methyl ester (Example 1, 400 mg.) in 20 ml. of isopropyl alcohol is cooled to 0° C. under nitrogen and a solution of sodium borohydride (0.2 g.) in 4 ml. of cold water is added. The mixture is stirred at 0° C. for 2.5 hrs., then 1 ml. of acetone is added and, 10 min. later, 1.2 ml. of glacial acetic acid. The organic solvents are removed by evaporation under reduced pressure and the residue is mixed with water and ethyl acetate. The organic extracts are washed with water and brine, dried over sodium sulfate, and concentrated to give a mixture of racemic 16-methyl-PGF$_{1\alpha}$ methyl ester and racemic 16-methyl-PGF$_{1\beta}$ methyl ester. This mixture is chromatographed on 150 g. of silica gel wet-packed with 30% ethyl acetate in cyclohexane, eluting with 500 ml. of 30%, 500 ml. of 50%, 500 ml. of 60%, 500 ml. of 70%, 1.5 l. of 80% and 1.0 l. of 90% ethyl acetate in cyclohexane, 5 l. of ethyl acetate, 1 l. of 5% and 1 l. of 20% methanol in ethyl acetate, taking 50 ml. eluate fractions. Those fractions shown by TLC to contain the desired products free of starting material and by-products are combined, then concentrated to give the Formula-VII PGF$_{1\alpha}$ - and PGF$_{1\beta}$ -type compounds, respectively, as their methyl esters.

A solution of racemic 16-methyl-PGF$_{1\alpha}$ methyl ester (0.15 g.) in a mixture of 4.5 ml. of methanol and 1.5 ml. of water is cooled to 5° C., and 0.6 ml. of 45% aqueous potassium hydroxide is added. The mixture is left standing 3.5 hrs. at 25° C., then is diluted with 75 ml. of water and extracted once with ethyl acetate to remove any neutral material. The aqueous layer is separated, made acid with dilute hydrochloric acid and extracted 4 times with ethyl acetate. The extracts are combined and washed 3 times with water, once with brine, dried over sodium sulfate, and evaporated to give racemic 16-methyl-PGF$_{1\alpha}$. Likewise, racemic 16-methyl-PGF$_{1\beta}$ methyl ester is saponified with aqueous potassium hydroxide and acidified to yield the free acid of racemic 16-methyl-PGF$_{1\beta}$.

Following the procedures of Example 4, each of the PGE$_1$-type compounds described in the paragraphs following Example 1 are transformed to the corresponding PGF$_{1\alpha}$ - and PGF$_{1\beta}$ -type esters and free acids, e.g. 16,16-dimethyl-PGE$_1$ ethyl ester yields 16,16-dimethyl-PGF$_{1\alpha}$ and -PGF$_{1\beta}$ ethyl esters and free acids.

EXAMPLE 5

Racemic 16-Methyl-PGA$_1$ Ethyl Ester and Free Acid (Formula VII: ⟩ is

R$_1$ is ethyl or hydrogen; R$_2$ is hydrogen; and R$_3$ is methyl)

Refer to Chart A.

I. Using hydrochloric acid. A solution of racemic 16-methyl-PGE$_1$ ethyl ester (400 mg.) in a mixture of tetrahydrofuran (5 ml.) and 0.5 N hydrochloric acid (5 ml.) is maintained under nitrogen at 25° C. for 5 days. The resulting mixture is diluted with one volume of brine and extracted with a mixture of diethyl ether and dichloromethane (3:1). The extract is washed with brine, dried, and evaporated. The residue (380 mg.) is dissolved in diethyl ether, and the solution is extracted with cold 5% aqueous sodium bicarbonate solution to give an aqueous layer A and a diethyl ether layer B. Aqueous layer A is acidified with dilute hydrochloric acid and then extracted with dichloromethane. This extract is washed with brine, dried, and evaporated to give the title compound free acid. Diethyl ether layer B is evaporated to give the title compound ethyl ester.

II. Using acetic acid. A solution of racemic 16-methyl-PGE$_1$ ethyl ester in a mixture of a glacial acetic acid (9 ml.) and water (1 ml.) is heated under nitrogen at 60° C. for 18 hrs. Then, the acetic acid and water are evaporated under reduced pressure, and the residue is chromatographed on 500 g. of acid-washed silica gel, eluting with a 25–100% gradient of ethyl acetate in Skellysolve B. The fractions containing the desired product free of starting material and by-products as shown by TLC are combined and evaporated to give the title compound ethyl ester.

Following the procedure of Example 5, each of the racemic PGE$_1$-type compounds described in the paragraphs following Example 1 are transformed to the corresponding PGA$_1$-type esters and free acids, e.g. 16,16-dimethyl-PGE$_1$ methyl ester yields 16,16-dimethyl-PGA$_1$ methyl ester.

Likewise following the procedure of Example 5, each of the haloethyl ester PGE$_1$-type compounds of and following Example 3 is transformed to the corresponding haloethyl ester PGA$_1$-type compound. Thereafter, following the procedure of Example 3, each of the haloethyl ester, PGA$_1$-type compounds is transformed with zinc, acetic acid, and water to the corresponding racemic free acid PGA$_1$-type compound. There is thus obtained racemic 16,16-dimethyl-PGA$_1$, 16-ethyl-PGA$_1$, 16,16-diethyl-PGA$_1$, and 16-ethyl-16-methyl-PGA$_1$.

EXAMPLE 6

Racemic 16-Methyl-PGA$_1$ Methyl Ester.

Refer to Chart B. A solution of the Formula-XI bismesylate of Example 1 (about 10 g.) in 75 ml. of acetone is mixed with 10 ml. of water and 20 ml. of saturated aqueous sodium bicarbonate solution. The mixture is heated at reflux under nitrogen for 4 hrs. Then, the mixture is cooled, acidified with 5% hydrochloric acid, and extracted with ethyl acetate. The extract is washed with brine, dried, and evaporated to give the title compound.

Following the procedure of Example 6, each of the bismesylates obtained after Examples 1 and 3 is transformed to the corresponding PGA-type ester, including the $\beta,\beta,\beta$-trichloroethyl esters. These are used for preparing the PGA-type free acids following the procedure of Example 3.

EXAMPLE 7

Racemic 16-Methyl-PGB$_1$ (Formula VII: ⌐) is

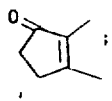

R$_1$ and R$_2$ are hydrogen; and R$_3$ is methyl).

The procedure shown in Chart A is followed. A solution of racemic 16-methyl-PGE$_1$ (Example 1, 200 mg.) in 100 ml. of 50% aqueous ethanol containing 10 g. of potassium hydroxide is kept at 25° C. for 10 hrs. under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washing with water and then with brine, dried, and evaporated to give the title compound.

Following the procedure of Example 7, 16,16-dimethyl-PGE$_1$ and -PGA$_1$ are each transformed to 16,16-dimethyl-PGB$_1$. washed Following the procedure of Example 7, the Formula-VII PGE$_1$-type and PGA$_1$-type compounds described above are transformed to the corresponding PGB$_1$ compounds.

EXAMPLE 8

16-Methyl-PGB$_1$ Methyl Ester.

A solution of diazomethane (about 0.5 g.) in diethyl ether (25 ml.) is added to a solution of 16-methyl-PGB$_1$ (50 mg.) in 25 ml. of a mixture of methanol and diethyl ether (1:1). The mixture is allowed to stand at 25° C. for 5 min. Then, the mixture is evaporated to give the title compound.

Following the procedure of Example 8, each of the other specific PGB$_1$-type, PGA$_1$-type, PGE$_1$-type, and PGF$_1$-type free acids defined above is converted to the corresponding methyl ester.

Also following the procedure of Example 8, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 16-methyl-PGB$_1$. In the same manner, each of the other specific PGB$_1$-type, PGA$_1$-type, PGE$_1$-type, and PGF$_1$-type free acids defined above is converted to the corresponding ethyl, butyl, 2-ethylhexyl, and cyclohexyl esters.

EXAMPLE 9

16-Methyl-PGE$_1$ Sodium Salt.

A solution of 16-methyl-PGE$_1$ (100 mg.) in 50 ml. of a water-ethanol mixture (1:1) is cooled to 5° C. and neutralized with an equivalent amount of 0.1 N aqueous sodium hydroxide solution. The neutral solution is evaporated to give the title compound.

Following the procedure of Example 9 but using potassium hydroxide, calcium hydroxide, tetramethylammonium hydroxide, and benzyltrimethylammonium hydroxide in place of sodium hydroxide, there are obtained the corresponding salts of 16-methyl-PGE$_1$.

Also following the procedure of Example 9 each of the PGE$_1$-type, PGF$_1$-type, PGA$_1$-type, and PGB$_1$-type acids defined above is transformed to the sodium, potassium, calcium, tetramethylammonium, and benzyltrimethylammonium salts.

The various examples given above describe the preparation of racemic intermediates and final products. Each of the intermediates and final products named and defined above is also obtained in each of the enantiomeric forms, d and l, by resolution of that compound or by resolution of an intermediate used to prepare that compound. For example, optically active 16-methyl-PGA$_1$ free acid is prepared by resolution of racemic 16-methyl-PGA$_1$ free acid (Example 5) or by dehydration as in Example 5 of optically active 16-methyl-PGE$_1$ free acid with the same absolute configuration. These resolutions are carried out by procedures known in the art, and may be used to obtain prostaglandinlike materials having the stereochemical configuration of the natural prostaglandins, other than at C-16, as typified by the following example.

EXAMPLE 10

16-Methyl-PGE$_1$ Methyl Ester Compounds having the Natural Configuration of PGE$_1$ except at C-16.

Refer to Chart B. There is first prepared bicyclic olefin VIII following the procedures of Example 1 but employing (2-methylhexyl)triphenylphosphonium bromide obtained from d-1-bromo-2-methylhexane. That d-isomer is obtained by methods known in the art, e.g. by resolving d-2-methylhexanoic acid (see P. A. Levene and L. W. Bass, Journal of Biological Chemistry 70, 211 (1926)), reducing that acid to the corresponding primary alcohol with lithium aluminum hydride, and converting that alcohol to the halide by reacting it with PBr₃, HBr, or any of the other halogenating agents known in the art to be useful for this purpose.

Next, the Formula-IX bicyclic intermediate is prepared, wherein $R_2$ is hydrogen; $R_3$ and $R_4$ are methyl; G is —$(CH_2)_3$—$CH_3$; and ~ is endo, following the procedures of Example 1. The 16-methyl Formula-IX compound is obtained as a mixture of diastereomers which are separated as follows. The mixture is chromatographed on a silica gel column (500 g) wet-packed with 5% ethyl acetate-Skellysolve B (one liter) and eluted with a 5 too 25% ethyl acetate gradient in Skellysolve B. Those fractions shown by TLC to contain the respective Formula-IX compounds are combined and evaporated to give the separate 8R and 8S Formula-IX compounds in which the stereochemistry at C-16 is the same as that of the d-isomer intermediate above.

Thereafter, following the procedures of Example 1, each of the above Formula-IX compounds is transformed to the Formula-X mixed glycols, thence to the Formula-XI bismesylates, and finally to a mixture of the Formula-XII 16-methyl-$PGE_1$ compound and the corresponding Formula-XII 15-epi-16-methyl-$PGE_1$ compound. Each mixture of $PGE_1$-type and 15-epi-$PGE_1$-type compounds is separated into the respective components by chromatography on a silica gel column (500 g.) wet-packed with 50% ethyl acetate-Skellysolve B (one liter), and eluted with 50% ethyl acetate-Skellysolve B, then ethyl acetate, and finally 10% ethanolethyl acetate. The more polar and less polar fractions shown by TLC to contain the $PGE_1$-type and 15-epi-$PGE_1$-type compounds, respectively, are combined separately and concentrated to yield the respective compounds.

Likewise following the above procedures, there is employed the (2-methylhexyl)triphenylphosphonium bromide obtained from 1-1-bromo-2-methylhexane. That l-isomer is obtained by methods known in the art from resolved l-2-methylhexanoic acid (See P. A. Levene and L. A. Mikeska, Journal of Biological Chemistry 84, 571 (1929)). There are finally obtained the respective optically active $PGE_1$-type and 15-epi-$PGE_1$-type compounds having a different configuration at C-16 than those obtained from the d-isomer intermediate above.

Of the above separated $PGE_1$-type compounds, those which are shown by smooth-muscle strip tests to have more biological response are the more useful compounds for the above-described purposes.

Following the procedures of Examples 10 and 3, and following Example 3, there are obtained the optically active 16-methyl-$PGE_1$ free acid compounds.

Following the procedures following Example 5, the optically active 16-methyl-$PGE_1$ compounds are transformed to the optically active 16-methyl-$PGA_1$ compounds.

Following the procedures of Example 4, the optically active 16-methyl-$PGE_1$ compounds are transformed to the optically active 16-methyl-$PGF_{1\alpha}$ and -$PGF_{1\beta}$ compounds.

Following the procedures of Example 7, the optically active 16-methyl-$PGE_1$ compounds are transformed to the optically active 16-methyl-$PGB_1$ compounds.

Following the procedures of Example 10 and of the above paragraphs following Example 10, but employing the 16-ethyl Formula-IX compounds instead of the 16-methyl Formula-IX compounds, there are obtained the corresponding optically active 16-ethyl-$PGE_1$, -$PGF_{1\alpha}$, -$PGF_{1\beta}$, -$PGA_1$, and -$PGB_1$ compounds.

EXAMPLE 11

Natural-Configuration 16,16-Dimethyl-$PGE_1$ Methyl Ester.

Refer to Chart B. The Formula-IX bicyclic intermediate wherein $R_2$, $R_3$ and $R_4$ are methyl; G is —$(CH_2)_3CH_3$; and ~ is endo is prepared following the procedures of Example 1.

The Formula-IX compound is then resolved as its optical isomers by the method of Corey et al., J. Am. Chem. Soc. 84, 2938 (1962), by reacting this keto compound with optically active L(+)-2,3-butanedithiol in the presence of p-toluenesulfonic acid. The diastereomeric ketals are separated on a preparative chromatographic column, and are then hydrolyzed separately to the Formula-IX bicyclic ketone, by methods known in the art, e.g. using 1:1 hydrochloric acid-water in tetrahydrofuran at 25° C. for 6 hrs. Thereafter, following the procedure of Example 1, each of the isomeric Formula-IX compounds is transformed to the corresponding Formula-XII compounds. The $PGE_1$ title compounds and 15-epi-$PGE_1$ compounds are separated following the procedures of Example 1, using silica gel chromatography. Because of the absence of asymmetry at C-16, the silylation step and subsequent chromatography are omitted for the 16,16-dimethyl compounds.

The optically active 16,16-dimethyl-$PGE_1$-type free acids are prepared following the procedures of Example 3, utilizing the haloethyl ester prepared from the separated Formula-IX compound above by the procedures of Example 2.

Following the procedures of Example 11, and of the above paragraph, but employing the appropriate 16,16-dialkyl Formula-IX compound as disclosed herein, there is obtained the corresponding optically active 16,16-dialkyl $PGE_1$ type compound, including the esters and free acids within the scope of $R_1$ as defined above.

Following the procedures outlined in Chart A and as set forth in Examples 4, 5, 6, and 7, the optically active 16,16-dialkyl-$PGE_1$ compounds disclosed herein are transformed to the corresponding optically active 16,16-dialkyl-$PGF_{1\alpha}$, $PGF_{1\beta}$, $PGA_1$, and $PGB_1$ type compounds, respectively. Thus, there are obtained optically active 16,16-dimethyl-$PGE_1$, -$PGF_{1\alpha}$, -$PGF_{1\beta}$, -$PGA_1$, and $PGB_1$; 16,16-diethyl-$PGE_1$, -$PGF_{1\alpha}$, -$PGF_{1\beta}$, -$PGA_1$, and -$PGB_1$; and 16-ethyl-16-methyl-$PGE_1$, -$PGF_{1\alpha}$, -$PGF_{1\beta}$, -$PGA_1$, and -$PGB_1$. There is obtained 16,16-dimethyl-$PGE_1$; mass spectral peaks (for trimethyl-silyl derivative) at 583, 499, and 409.

We claim:

1. An optically active compound of the formula

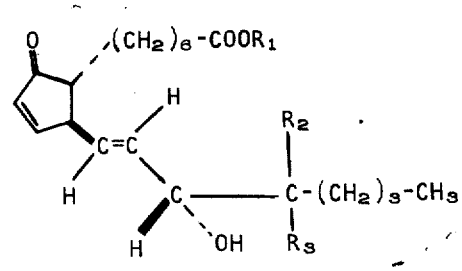

or a racemic compound of that formula and the mirror image thereof, wherein $R_1$ is hydrogen, alkyl of one to 8 carbon atoms, inclusive, or a pharmacologically acceptable cation, and wherein $R_2$ and $R_3$ are methyl or ethyl.

2. An optically active compound according to claim 1.

3. A racemic compound according to claim 1.

4. 16,16-Dimethyl-PGA$_1$, an optically active compound according to claim 1 wherein $R_1$ is hydrogen, and $R_2$ and $R_3$ are methyl.

5. Racemic 16,16-dimethyl-PGA$_1$, a compound according to claim 1 wherein $R_1$ is hydrogen, and $R_2$ and $R_3$ are methyl.

6. 16,16-Dimethyl-PGA$_1$, methyl ester, an optically active compound according to claim 1.

* * * * *